United States Patent [19]
Kullas et al.

[11] Patent Number: 5,147,292
[45] Date of Patent: Sep. 15, 1992

[54] CONTROL HANDLE WITH LOCKING MEANS FOR SURGICAL IRRIGATION

[75] Inventors: Karen E. Kullas, Taunton; Bruce E. Newcomb, Berkley, both of Mass.

[73] Assignee: C. R. Bard, Inc., Murray Hill, N.J.

[21] Appl. No.: 650,688

[22] Filed: Feb. 5, 1991

[51] Int. Cl.⁵ .................................. A61M 1/00
[52] U.S. Cl. ..................... 604/34; 604/250; 604/902; 128/66
[58] Field of Search .......... 604/27, 34, 35, 39, 604/43, 84, 250, 902; 433/80, 88, 89, 91, 95, 96, 141, 216; 128/66

[56] References Cited

U.S. PATENT DOCUMENTS

| | | | |
|---|---|---|---|
| 3,635,251 | 1/1972 | Gaines | 137/636 |
| 3,698,681 | 10/1972 | Lacey | 251/10 |
| 4,245,812 | 1/1981 | Burger | 251/10 |
| 4,273,260 | 6/1981 | Bush | 604/250 |
| 4,519,385 | 5/1985 | Atkinson et al. | 128/66 |
| 4,941,872 | 7/1990 | Felix et al. | 604/27 |
| 5,046,486 | 9/1991 | Grulke et al. | 128/66 |

*Primary Examiner*—John D. Yasko
*Attorney, Agent, or Firm*—Wolf, Greenfield & Sacks

[57] ABSTRACT

A handpiece for a surgical irrigator and suction device includes a drip-free valve arrangement in which the portion of the flexible irrigation conduit is kinked in a V-shape. The extent to which the flexible irrigation conduit is kinked is controlled by a trigger, adapted for one-hand operation and in which the trigger can be controlled to be locked, selectively, in a full flow, no flow or manually controllable variable flow mode.

6 Claims, 6 Drawing Sheets

CONTROL HANDLE WITH LOCKING MEANS FOR SURGICAL IRRIGATION

FIELD OF THE INVENTION

This invention concerns a handpiece for a surgical irrigation and suction device.

BACKGROUND OF THE INVENTION

It is important during surgical or emergency procedures that the wound or surgical site be maintained clean and antiseptic. Among the common techniques for maintaining a clean surgical site is to irrigate the site with an irrigation or antiseptic solution. Typically the antiseptic solution will be supplied from a reservoir through tubing to a dispensing handle which is manipulated by the surgeon or a surgical assistant. Removal of the irrigation solution as well as other fluids which may collect at the surgical site is removed by applying a suction instrument in the region to withdraw the fluids. The suction instrument may be manipulated by the surgeon or by a surgical assistant.

U.S. Pat. No. 4,941,872 relates to an improved handle that is connectible to sources of irrigation fluid and suction and which has detachable and interchangeable suction and irrigation fittings. The handle incorporates a spring-biased trigger and a non-leaking valve mechanism which throttles the outlet for the irrigation flow to provide a flow control.

The handle is formed from a pair of mateable plastic sections which house a suction conduit and an irrigation conduit. The proximal end of the handle includes means to connect tubes from a suction source and irrigation fluid source, respectively, to the suction and irrigation conduits within the handle. The distal end of the handle is provided with sockets to receive, detachably, a suction wand and an irrigation wand.

A trigger-operated valving mechanism is incorporated into the handle in a manner which provides a leak-proof, drip-free, controlled release for the irrigation fluid. The valving mechanism includes a flexible tube which defines a portion of the irrigation conduit. The valving mechanism includes an arrangement in which the flexible tube is drawn into a V-shaped kinked configuration by a closure member which fully and completely closes off all flow through the tube and in a manner which avoids leaking or dripping. A spring is connected to a trigger which, when squeezed, shifts the position of the spring to release the king and permit liquid flow. The spring normally biases the device in a closed, no-flow, position. The degree to which the trigger is squeezed controls the degree to which the irrigation flow channel is opened.

It has been discovered that is some instances it would be desirable to provide an arrangement for locking the trigger mechanism in a configuration in which the irrigation fluid flows fully without requiring the physician or assistant to manually and continually squeeze the trigger against the spring biasing force. It is among the general objects of the invention to provide an improved handle having a trigger that is lockable and unlockable in one hand operation.

SUMMARY OF THE INVENTION

In accordance with the invention, the trigger is constructed to be lockable to maintain the device in an open, full flow position. The trigger is constructed to enable the user to lock the device in the full flow position or, alternatively, to permit manually controllable, infinitely adjustable flow. The trigger is molded from a suitable plastic material to have a rigid portion and a deformable, flexible portion that defines a trigger extension. The trigger is pivotably mounted, by its rigid portion, to the handle housing with the rigid portion being engageable with the spring and the element that engages and draws the flexible tube to its V-shaped kinked configuration. The flexible trigger extension is resiliently deformable with respect to the rigid portion of the trigger and is arranged so that it can be deformed toward a portion of the handle housing. The flexible trigger extension is further constructed to be self-biasing toward an unlatched position such that when the trigger is squeezed, the latch automatically unlocks, thereby freeing the trigger for full manual control. The trigger and trigger extension are constructed to be easily operated by one hand by the physician or an assistant.

It is among the objects of the invention to provide an improved arrangement for a hand held surgical irrigation and suction device.

Another object of the invention is to provide surgical irrigation handpiece with an improved valving and trigger mechanism to provide controlled release of irrigation fluid.

A further object of the invention is to provide a surgical irrigation handpiece that is adapted for one hand operation and can be operated selectively in a fully off, no flow configuration or a locked, full flow configuration or a manually operable, variable flow configuration.

Another object of the invention is to provide surgical irrigation device that will not drip or leak when released.

A further object of the invention is to provide a device of the type described which is reliable yet is of simple and inexpensive construction and lends itself to one time, disposable use.

DESCRIPTION OF THE DRAWINGS

The foregoing and other objects and advantages of the invention will be appreciated more fully from the following further description thereof, with FIG. 1 is an illustration of the control handle with suction and irrigation wands attached

DESCRIPTION OF THE PREFERRED EMBODIMENT

Figure 1:
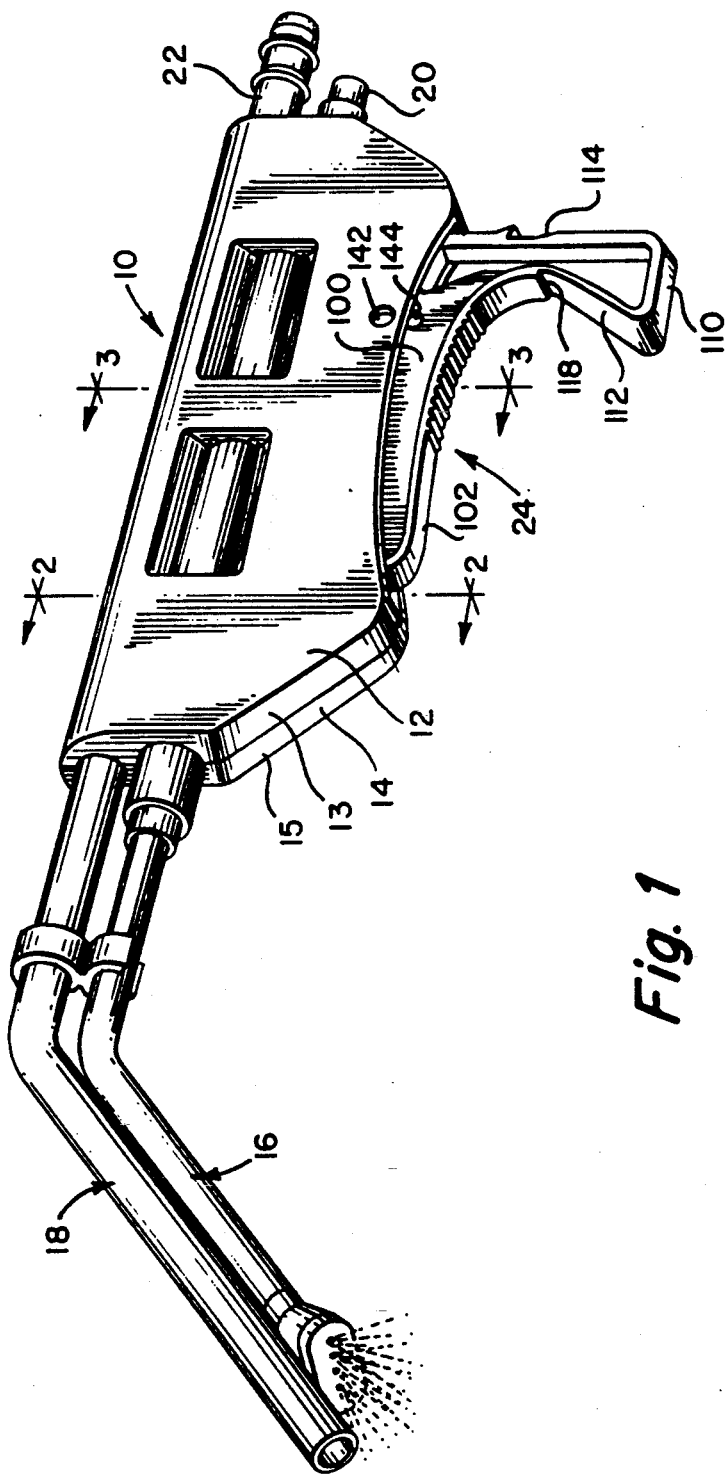

As shown in FIG. 1 the handle 10 may be formed from a pair of molded plastic side panels which may be referred to, for convenience of description, as a left side panel 12 and a right side panel 14. The side panels 12, 14 are molded with a plurality of internal ribs, grooves and other supporting members which receive the various internal parts of the device and sandwich the various internal parts together. The side panels 12, 14 are provided with peripheral walls 13, 15 which meet edge-to-edge when the panels 12, 14 are brought together. The meeting edges of the peripheral walls 13, 15 are secured together as by adhesive, ultrasonic welding or the like.

The internal arrangement of the panels 12, 14 and operating elements incorporated therein is illustrated and described in detail in said U.S. Pat. No. 4,941,872, to which reference is made and which is hereby incorporated by reference in its entirety.

A suction wand 18 and an irrigation wand 16 are detachably connectable to and extend forwardly from the front end of the handle 10. The rear end of the handle 10 is connectable to an irrigation fluid tube 20 which is connectable to a source of irrigation fluid and a suction tube 22 which is connectable to a source of suction. Passageways are formed internally through the handle 10 to communicate irrigation fluid inlet tube 20 with the irrigation wand 16 and the suction tube 22 with the suction wand 18 respectively. The device also includes a trigger 24 which normally projects downwardly through an opening in the bottom of the handle 10. The trigger 24 operates a valve and throttling mechanism within the handle to open and close the irrigation fluid passageway and to throttle and variably control the rate of fluid flow.

The handle includes an irrigation conduit defined by a flexible plastic tube 38 which is confined within a longitudinally extending channel 40. The tube 38 preferably is formed from a material having relatively high elastic memory and may be formed, for example, from silicone rubber. The channel 40 serves the additional purpose of preventing the plastic tube 38 from expanding beyond the confines of the channel 40. This is particularly desirable when the device is to be used with a pulsating irrigation fluid delivery system. The tube 38 is secured at its front and rear ends as described in U.S. Pat. No. 4,941,872 to provide a secure connection to fittings 44, 50 which serve to connect the handle to the source of irrigation liquid and to the distribution nozzle 16.

Figure 5:
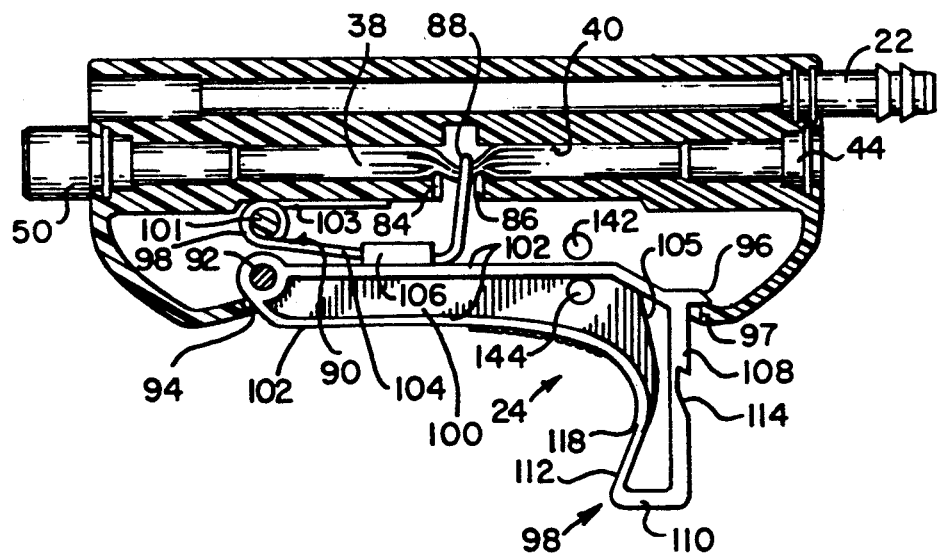
FIG. 5 is a partly sectional side elevation of the device with one side of the handle removed and with the trigger released so that the flexible irrigation tube is kinked in a closed, no-flow configuration.
Figure 6:
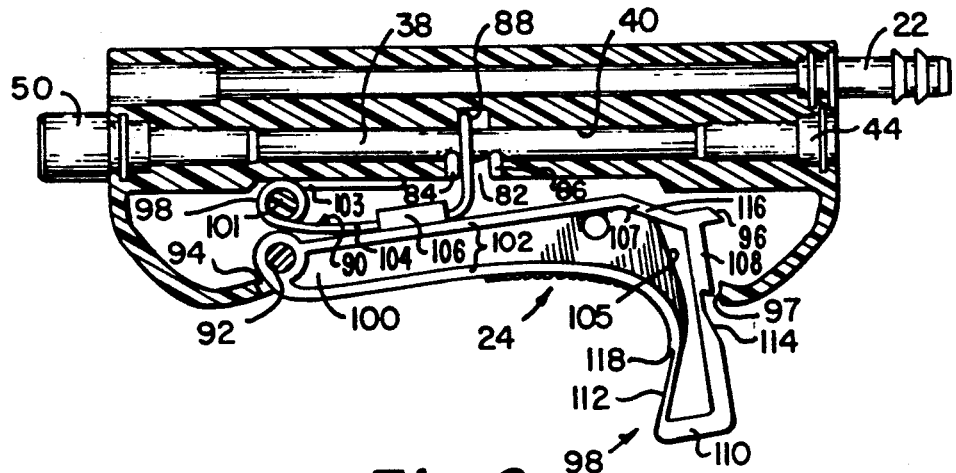
FIG. 6 is an illustration similar to FIG. 5 but with the trigger depressed to a full flow configuration.

Flow of irrigation fluid normally is shut off by an arrangement which forms a V-shaped kink in the flexible tube 38. Kinking of the tube is controllably released by squeezing the trigger 24. As shown in FIGS. 5 and 6 an intermediate portion of the tube 38 passes over an aperture 82 that intersects the channel containing the flexible tube 38. The aperture 82 is defined by a pair of longitudinally spaced, transversely extending ribs 84, 86. The portion of the tube 38 which spans the opening 82 is drawn shut by a closure member in the form of a hook 88 which partially circles the tube 38 between the ribs 84, 86. The hook 88 is biased downwardly to draw the spanning segment of the tube 38 downwardly and partly into the aperture 82 thus partially wrapping the tube 38 about the ribs 84, 86. That draws the tube 38 firmly against the upper edges of the ribs 84, 86 to pinch the tube as both of those locations. It also causes a third pinchign of the tube 38 by the hook 88 at a location between the ribs 84, 86.

The hook 88 preferably is formed integrally with a spring 90 which is arranged to bias the hook 88 in a downward direction, to bias the tube 38 shut. The spring 90 also serves to provide a spring resistance for the trigger 24. The trigger 24 extends generally longitudinally of the housing 10. The trigger 24 is pivoted, at its forward end, to a pivot post 92 formed integrally with and extending from one of the panels, such as the right panel 14. The peripheral walls 13, 15 of the panels 12, 14 are cut away along the lower portion to define a slot 94 through which the trigger 24 projects. The spring 90 is arranged to bias the trigger in a direction which extends out of the slot 94. The rear end of the trigger has an integrally formed stop member 96 which engages a ledge 97 formed at the back end of the peripheral wall just rearwardly of the slot 94 to limit and define the maximum extent to which the trigger 24 projects out of the slot 94.

The spring 90 has a wound portion 98 which is mounted about transversely extending spring support post 101. The spring includes a tail portion 103 which extends from the coiled portion 98 and is captured by engagement with the underside of the channel for receiving tube 38. The spring 90 also includes a rearwardly extending trigger portion 104 which extends from the other end of the spring coil 98. The trigger portion 104 bears against the upper surface of the trigger 24, rearwardly of the pivot 92 to bias the trigger 24 downwardly. The upper surface of the trigger 24 preferably is provided with a pair of spring guide tabs 106 which embrace the trigger spring portion 104 and maintain it in engagement with the upper surface of the trigger 24.

The hook portion 88 is formed integrally with the spring as an extension from the end of the trigger spring portion 104. The trigger spring portion 104 terminates below the spaced ribs 84, 86 and the hook portion 88 extends upwardly through the aperture 82 to wrap about and engage the tube 38. Thus, the spring 90 serves to draw the tube in a v-shaped, kinked and closed configuration while simultaneously biasing the trigger 24 toward its normal position. As shown in FIG. 6 when the trigger 24 is squeezed the hook 88 is raised to release the kinking effect on the tube 38 and to permit flow of liquid through the tube. The degree to which the trigger is depressed controls the extent to which the tube 38 is opened to flow.

Figure 7:
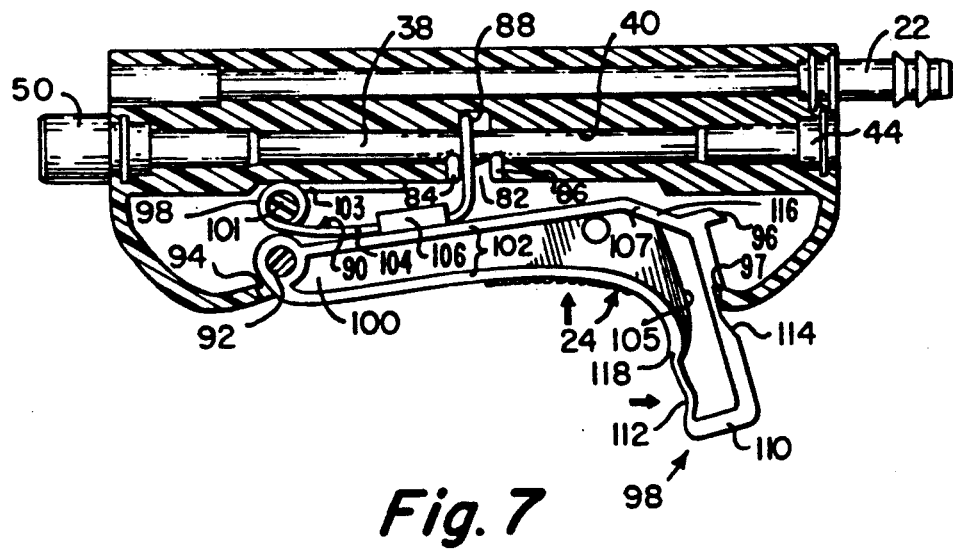
FIG. 7 is an illustration similar to FIG. 6 in which the deformable trigger extension has been deformed to a position to lock the device in its open, full flow position.
Figure 8:
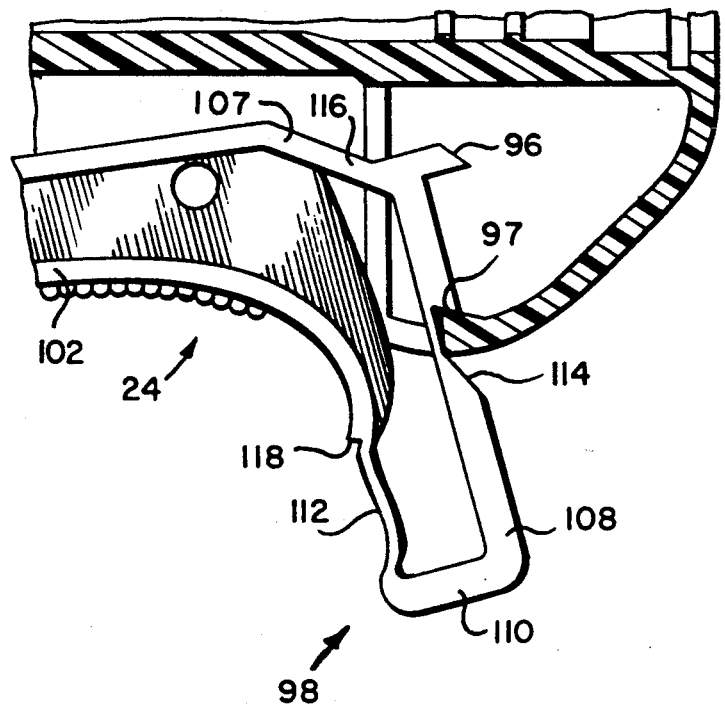
FIG. 8 is an enlarged illustration of the latching elements of the handle and the trigger extension.

In accordance with the invention, the trigger 24 may be operated in three modes, including a fully released mode (FIG. 5) in which the trigger 24 is released with the stop member 96 in engagement with the ledge 97 such that the hook 88 draws the tube 38 into its V-shaped, kinked and closed configuration. In a second mode, the trigger 24 may be squeezed to the degree desired by the physician to provide an infinitely adjustable flow of liquid through the tube 38 (FIG. 6). In a third mode, illustrated in FIG. 7, the trigger 24 may be locked in a fully squeezed, full flow position. For this purpose, the trigger 24 preferably is injection molded from a suitable plastic material such as polypropylene and is provided with a resilient, flexible extension, indicated generally at 98, which may be deformed into the locked position as shown in FIG. 7. The trigger 24 preferably is formed to include a forward, rigid section and the rearward flexible trigger extension 98. The forward, rigid section is defined by a central rigidifying web 100 that is formed integrally with a peripheral flange 102. The rearward portion of the flange 102 is extended to form and define the trigger extension 98. The central web 100 terminates at a rear end 105 and is unconnected to those portions of the continuation of the flange 102 that define the trigger extension 98. Thus, the continuation of the flange 102 that defines the trigger extension is unsupported, is not rigidified by the web 100 and, consequently, is flexible and resilient.

More specifically, the trigger extension 98 includes a top segment 107, a rear segment 108 that extends rearwardly of and downwardly from the rear end of the top segment 107, a bottom segment 110 and a web segment 112. The bottom segment 110 is connected to and extends forwardly from the lower end of the rear segment 108. The web segment 112 extends between the forward end of the bottom segment 110 and the rear end of the lower portion of the flange 102. Thus, in the illustrative embodiment of the invention segments 107, 108, 110 and 112 define a continuous flexible and resilient loop flexibly attached to the rigid portion of the trigger.

The rearwardly facing surface of the rear segment 108 is provided with a notch 114 adapted to engage the ledge 97 on the handle. Thus, the trigger extension 98 attached to the rigid portion of the trigger at an upper juncture 116, where the top segment 107 separates from the rear end 105 of the web and at a lower junction 118, where the upper end of the web segment 112 is connected to the lower portion of the flange 102. The upper juncture 116 and lower juncture 118 serve as living hinges. The plastic material, from which the trigger 24 is formed is selected and the device is dimensioned so that the trigger extension 98 can be flexed rearwardly, about the junctures 116, 118, to a position in which the notch 114 can engage the ledge 97, as illustrated in FIG. 7. When flexed into the locked position of FIG. 7, the web segment 112 is distorted rom tis relaxed configuration shown in FIGS. 5 and 6. It will be appreciated that in order for the physician to lock the device in the fully opened configuration as shown in FIG. 7, he need only squeeze the trigger 24 and simultaneously urge trigger extension 98 rearwardly. Once the notch 114 has engaged the ledge 97, the trigger may be released and the force of the spring 90 will maintain the notch 114 in engagement with the ledge 97.

The surfaces of the notch 114 are shaped to maintain the engagement of the notch 114 with the ledge 97 when under the influence of the spring 90. In order to release the trigger from its locked configuration, the physician need only further depress the trigger to raise the upper surface 120 of the notch 114 from out of engagement with the ledge 97. Once released, the inherent resilience of the web segment 112 and the region of the upper juncture 116 will return the trigger extension 98 to its relaxed configuration, as suggested in FIG. 6. In its relaxed configuration, the notch 114 and rear segment 108 are clear of the ledge 97 (FIG. 6), thus returning the device to manual operation. The physician then may manually control the fluid flow or may release the trigger entirely to permit it to return to a fully closed position (FIG. 5).

Figure 9:
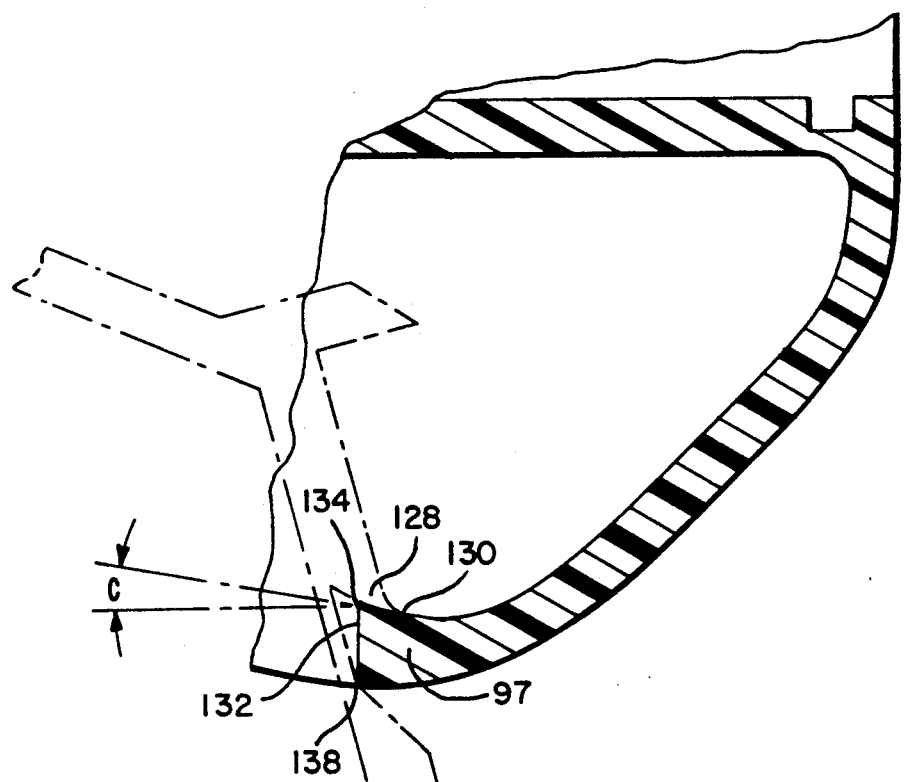
FIG. 9 is an enlarged illustration of the trigger and housing with the trigger extension in a latched configuration.
Figure 10:
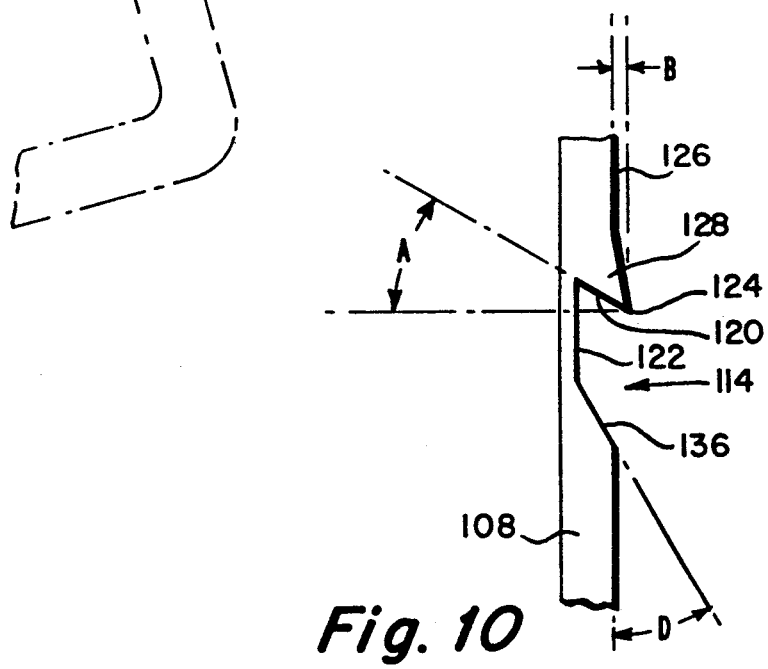
FIG 10 is an enlarged detailed illustration of the shape of the notch region on the trigger extension.

FIGS. 9 and 10 illustrate, in enlarged detail, a desired configuration for the ledge 97 and the notch 114. As shown in FIG. 10, the notch 114 includes an upper surface 120 and a forward surface 122. The upper surface 120 is inclined at an angle A with respect to a perpendicular to the length of the rear segment 108. The rearward edge of the surface 120 terminates at a transverse edge 124. The surface 120 may be extended slightly rearwardly of the rearwardly facing surface 126 of the segment 108 to locate the edge 124 slightly rearwardly of the surface 126 by an amount indicated at B. By way of example, angle A may be of the order of 30° and B may be of the order of 0.020". The trigger extension thus may be considered as having a rearwardly and downwardly extending finger 128. The cross section of the finger 128 tapers toward the edge 124 and may be somewhat flexible as it approaches the edge 124.

The ledge 97 is formed to include an upper surface 130 and a forwardly facing surface 132 which meet at a relatively sharp corner 134. The upper surface 130 of the ledge 97 is formed and oriented with respect to the trigger 24, the path of movement of the trigger and, particularly, the path and range of movement of the trigger extension 98, so that the notch 114 can be brought into engagement with the ledge 97 as shown in FIG. 9. When in engagement, the ledge 97 is received within the notch 114 and against the upper surface 130 of the ledge 97. The angle A of the surface 120 and the angle C (about 10°) that the surface 130 makes with the horizontal are such that there is no tendency for the finger 128 to slip off of the ledge 97. The force of the spring urging the trigger downwardly about pivot 92 maintains the latching engagement of the finger 128 with the surface 130. The force of the spring 90 is sufficient to overcome the resilience of the trigger extension 98.

The notch 114 includes a lower surface 136 that forms a relatively shallow angle D with the rear surface 126 of the segment 108. The angle D preferably is less than the angle A and defines a relatively wide mouth for the notch 114 to receive the ledge 97. Surface 136, if brought to bear against the lower forward edge 138 of the ledge 97, can guide the notch 114 onto and about the ledge 97 into proper engagement.

Thus, when the trigger extension is raised and flexed rearwardly, the edge 124 and upper surface 120 of the notch engage the upper surface 130 of the ledge 97. The foregoing configuration assures that the trigger extension and ledge will not inadvertently slip out of engagement.

The foregoing configuration for the trigger extension is desirable in that it provides simple, comfortable and convenient one-handed operation for the physician. By providing the web segment 112 and forming it so that it defines substantially a continuous substantially smooth extension of the lower portion of the flange 102. A smooth tactile surface is provided for the physician. The resilience of the web segment 112 adds to the resilience of the top and rear segments 107, 108, to assure that there will be sufficient resilience to snap the notch 114 out of engagement with the ledge 97 when the trigger 24 is squeezed to release the finger 128. The continuous loop configuration, including the connection of the web segment 112 enables the trigger extension 98 to flex as a unit and avoids development of excess bending stresses at the relatively thin regions of The notch. The web 112 therefore, aids in maintaining the trigger extension in its desired shape through many repetitive cycles, substantially more than those that ordinarily would be expected to occur during a typical use of the device. The trigger extension 98 projects substantially below and beyond the envelope of the housing so that it is easily and readily available to the physician. The configuration of the device provides for a smooth, desirable tactile response even when the user is wearing surgical gloves.

Figure 4A:
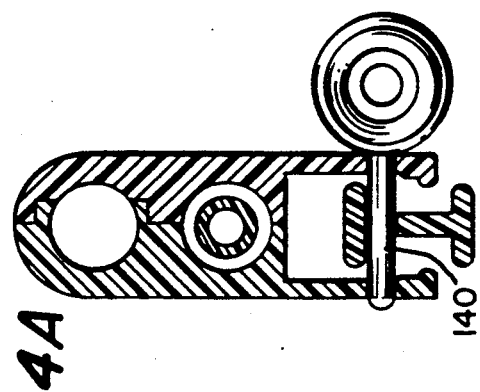
FIG. 4A is a sectional illustration taken through the retaining pin as seen along the line 4A—4A of FIG. 4.
Figure 3:
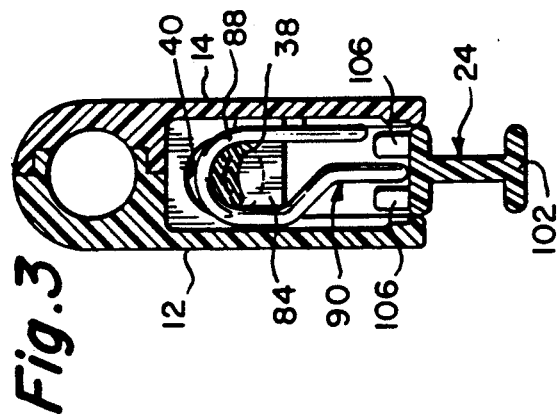
FIG. 3 is a sectional view of the handle as seen along the line 3—3 of FIG. 1 and illustrating the manner in which the flexible irrigation tube is kinked shut by the valving device.
Figure 2:
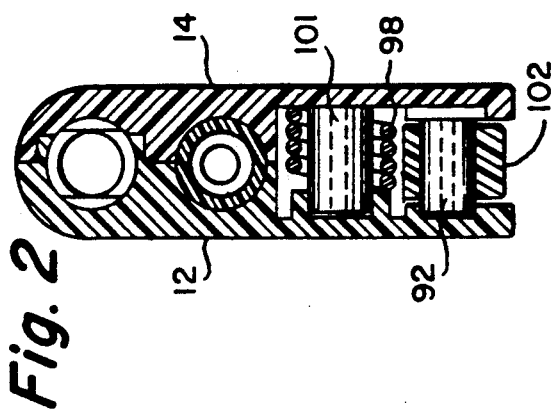
FIG. 2 is a sectional illustration of the handle as seen along the line 2—2 of FIG. 1.
Figure 4:
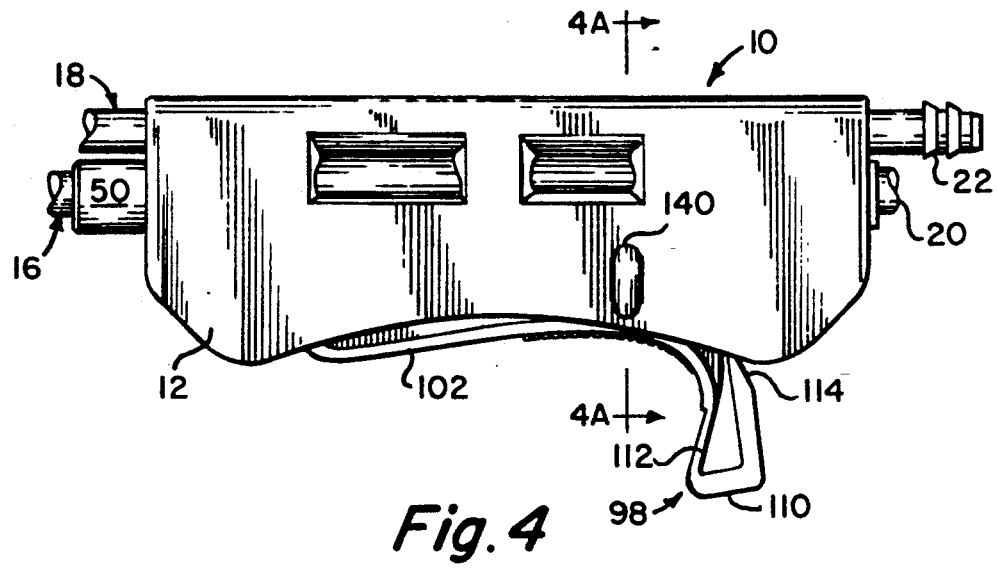
FIG. 4 is a side elevation of the handle with the trigger depressed in a full flow configuration and retained by a retaining pin in that configuration.

In another aspect of the invention it is preferred to provide a temporary locking arrangement for securing the handle in an open position, independently of the latching arrangement associated with the trigger extension. The temporary latching arrangement is desirable in order that the device may be sterilized, shipped and stored with the hook 88 out of engagement with the flexible conduit 38, so as not to cause the flexible conduit to take on a permanently kinked set. It is desirable to do so independently of the trigger extension latching arrangement in order that the trigger extension also does not take on a permanent set. To that end and as shown in FIGS. 4 and 4A, the device is provided with a pin 140 that is intended to be passed through aligned holes 142 and 144 in the housing and rigidifying web 100 of the rigid portion of the trigger. The holes 142 and 144 are arranged to be aligned when the trigger is in an open position. The pin 140 is passed through the aligned holes to retain the device in that configuration during sterilization, shipment and storage.

From the foregoing, it will be appreciated that the invention provides a new and improved trigger arrangement for a control handle of a surgical irrigation device. The arrangement provides a relatively large, easily engaged trigger extension that is operable with one hand. The device provides a smooth and continuous surface along which the trigger and extension may be squeezed.

It should be understood that the foregoing description of the invention is intended merely to be illustrative thereof and that other embodiments, modifications and equivalents may be apparent to those skilled in the art without departing from its spirit.

Having thus described the invention what we desire to claim and secure by Letters Patent is:

1. A handpiece for a surgical irrigator comprising:
   a handle body;
   a flexible fluid conduit extending through the body for connection at one end to a source of irrigation fluid and at the other end of a fluid outlet;
   a closure member engageable with a portion of the flexible conduit and being movable with respect tot he conduit to variably constrict the flow passage through the conduit, thereby to variably control or shut off flow through the conduit;
   a trigger movably mounted to the handle body and connected to the flow control member for controlling the extent to which the passage through the flexible conduit is constricted;
   means biasing the trigger toward a position in which the flexible conduit is fully closed whereby the trigger may be squeezed to variably open the flexible conduit;
   the trigger including a relatively rigid portion and a relatively flexible portion, the flexible portion defining a trigger extension that projects substantially out of the housing, the trigger extension including a latch element selectively engageable with a portion of the housing to latch the trigger in an open position.

2. A handpiece for a surgical irrigator as defined in claim 1 wherein the handle includes a forward end and a rearward end;
   the forward portion of the trigger defining a relatively rigid portion and being pivoted to the handle body;
   the trigger extension being formed at the rearward portion of the trigger.

3. A handpiece for a surgical irrigator as defined in claim 2 wherein the trigger extension comprises:
   a continuous loop element formed integrally with and extending from the rearward end of the rigid portion of the trigger and extending rearwardly and downwardly of the trigger;
   the interior of the loop being unsupported whereby the segments defining the loop may flex about their points of connection to the rigid portion of the trigger;
   a latching element formed in the loop element and being positioned so that when the trigger is moved to its open configuration the latching element will be disposed opposite said portion of the housing;
   the connection between the loop element and the rigid portion of the trigger being sufficiently flexible so that the loop portion may be flexed rearwardly thereby to cause engagement of the latching element with the portion of the housing.

4. A handpiece for a surgical irrigator as defined in claim 3 wherein the trigger extension further comprises:
   the continuous loop element including a downwardly extending rearward segment, a forwardly extending bottom segment and a relatively thin web segment extending form the forward end of the bottom segment to the rearward end of the lower surface of the trigger.

5. A handpiece for a surgical irrigator as defined in any one of claims 1–4 wherein the latching element comprises a notch formed on the trigger extension at a location adapted to engage said portion of the housing.

6. A handpiece for a surgical irrigator as defined in claim 1 further comprising means for temporarily locking the trigger in an open position independently of the trigger extension.

* * * * *